(12) United States Patent
Saari et al.

(10) Patent No.: US 6,429,333 B1
(45) Date of Patent: Aug. 6, 2002

(54) METHOD FOR PREPARING FORMIC ACID

(75) Inventors: Kari Saari, Vantaa; Esko Tirronen, Espoo; Antti Vuori, Helsinki; Marko Lahtinen, Pori, all of (FI)

(73) Assignee: Kemira Chemicals Oy, Helsinki (FI)

( * ) Notice: Subject to any disclaimer, the term of this patent is extended or adjusted under 35 U.S.C. 154(b) by 0 days.

(21) Appl. No.: 09/868,514

(22) PCT Filed: Dec. 21, 1999

(86) PCT No.: PCT/FI99/01060

§ 371 (c)(1),
(2), (4) Date: Jun. 19, 2001

(87) PCT Pub. No.: WO00/39067

PCT Pub. Date: Jul. 6, 2000

(30) Foreign Application Priority Data

Dec. 23, 1998 (FI) .................................................. 982801

(51) Int. Cl.[7] .......................... C07C 53/02; C07C 53/04; C07C 53/06
(52) U.S. Cl. ....................................... 562/609; 562/609
(58) Field of Search ........................................... 562/609

(56) References Cited

U.S. PATENT DOCUMENTS 5,405,992 A  *  4/1995  Funk et al.

FOREIGN PATENT DOCUMENTS

| DE | 3220555 | * 11/1983 |
| EP | 596484 | * 5/1994 |

* cited by examiner

Primary Examiner—Johann Richter
Assistant Examiner—Farhad Forohar
(74) Attorney, Agent, or Firm—Swidler Berlin Shereff Friedman, LLP

(57) ABSTRACT

In a method for preparing formic acid, methyl formate is prepared with methanol as a reactant. In the method, methyl formate obtained from methanol in a reaction is fed through an ion exchange bed, in which the hydrolysis into formic acid and methanol and the separation of formic acid from methanol take place simultaneously by means of the catalytic and adsorbent properties of a solid in exchange material in the ion exchange bed

14 Claims, 5 Drawing Sheets

METHOD FOR PREPARING FORMIC ACID

This application is a 371 of PCT/FI99/01060 filed on Dec. 21, 1999 claiming priority on Finland 982801 filed on Dec. 23, 1998.

The present invention relates to a method for preparing formic acid, the method being based on preparing methyl formate with methanol as the reactant and on acid-catalyzed hydrolysis of methyl formate, which is a so-called equilibrium reaction. Methyl formate can be prepared at the beginning of the process from carbon monoxide and methanol. In addition to formic acid, the hydrolysis of methyl formate produces methanol which is circulated back to the preparation of methyl formate.

The hydrolysis of methyl formate is normally carried out in a pressure reactor on the basis of homogeneous acid catalysis, wherein an acid solution is used as a catalyst and/or the autocatalytic nature of the hydrolysis reaction is utilized; that is, the produced formic acid is used as the catalyst. To obtain sufficient conversion, the hydrolysis is carried out at a temperature of about 120° C. and under a pressure of about 10 bar. At such high temperatures, a high pressure is necessary to prevent evaporation of the reaction mixture, because the hydrolysis reaction will only take place in the liquid phase.

The reaction mixture is led into a distillation column where the mixture of methyl formate and methanol is separated from the mixture of water and formic acid. Methyl formate and methanol are separated from each other in a separate methyl formate circulation column, and they are both returned to the process. Formic acid is concentrated in several successive distillation columns, and the separated water is circulated back to the hydrolysis stage (Hase, A., Koppinen, S., Riistama, K., Vuori, M.: Suomen kemianteollisuus, pp. 53–54, Chemas Oy, 1998).

The majority of the costs in the above-presented process are caused by energy consumption at the distillation stages (water separation) and the reverse reaction of formic acid to methyl formate and water during the first distillation stage. The conversion of methyl formate obtained in the process is low, due to the equilibrium nature of the reaction and the reverse reaction.

In principle, the above-mentioned costs can be reduced either by producing more concentrated formic acid at the hydrolysis stage and/or by preventing the reverse reaction of formic acid. The hydrolysis of methyl formate as an equilibrium reaction at different temperatures and under different pressures is well known, and consequently it is not possible to affect the economy of the process by varying the temperature and the pressure to a great extent.

The separation of reaction products from each other in a reaction mixture has been examined in an annular chromatographic reactor filled with activated carbon (Cho, B. K.: Studies of Continuous Chromatographic Reactors, Dissertation Thesis, University of Minnesota, 1980) and in a conventional tubular chromatographic reactor filled with activated carbon (Wetherhold, R. G., Wissler, E. H., Bischoff, K. B.: An Experimental and Computational Study of the Hydrolysis of Methyl Formate in a Chromatographic Reactor, Chemical Reaction Engineering, 1974: 133, 181–190) by using as an eluent 0.5 to 1.0 M hydrochloric acid HCl which also acts as a catalyst in the reaction. With low feeding concentrations of methyl formate, it was possible to achieve conversions of even 100%, but in this case also the concentration of produced formic acid remained relatively low in view of its economic exploitation.

In this way, separation and concentration of methanol was achieved in both cases, but concentration of formic acid could be attained only in the latter reactor. However, this application involves the problem that the acid catalyst must be separately added into the system and separated after the reaction.

Also known is the hydrolysis of methyl formate by using a heterogeneous catalyst. Thus, a solid catalyst is used as the catalyst instead of an acid solution. In practice, this means a porous, strongly acidic polystyrene divinyl benzene (PS-DVB) based cation exchange resin (EP patent 596 484, SU inventor's certificate 1085972) with sulphonic acid as the functional group. It is possible to use both a macroporous and a gel-like cation exchanger. In this application, a weakly acidic cation exchanger was not found to have the catalytic property.

Using a heterogeneous catalyst, the advantage is achieved that the catalyst can be easily separated from the reaction mixture after the reaction. Such a hydrolysis can be carried out both in a batch-type stirred and pressure reactor. The separation of formic acid can be performed by conventional distillation after the reaction from the whole reaction mixture or in connection with the reaction (reactive distillation).

However, it is not possible in a stirred reactor or a conventional pressure sure reactor to utilize the property of the ion exchange resin to separate the reaction products, and thus no conversions greater than the equilibrium conversion are achieved. This property is based on the fact that different compounds are adsorbed with different affinities onto the surface of various adsorbent materials. For example, activated carbon and strongly acidic cation exchange resin have very different adsorption properties with respect to the compounds in question.

The final result of the hydrolysis stage, particularly the formic acid concentration, is significantly affected by the composition of the reaction mixture at the initial stage. Depending on the implementation of the process, the water/methyl formate ratio varies to a great extent. It can be for example 0.3:3, 14:1, 1:1.5, 1.5:1, or 1:1.

Now, it has been observed that it is possible to reduce both of the above-mentioned costs (energy consumption in water separation by distillation and the reverse reaction of formic acid to methyl formate) simultaneously by shifting the equilibrium of the reaction towards the reaction products, i.e. formic acid and methanol. In practice, this means separation of the reaction products from each other in the reaction mixture and concentration of these components. This is possible in a chromatographic reactor, which is a certain type of a tubular reactor and which is filled with a suitable solid material. The reactant mixture, containing methyl formate and water, is supplied into the reactor, and a reaction mixture is received from the reactor. This mixture usually contains unreacted reactants in addition to the reaction products.

It is an aim of the present invention to simultaneously utilize not only the catalyzing property of a strongly acidic ion exchange resin but also its property to separate different components of a reaction mixture by performing the hydrolysis of methyl formate in a chromatographic reactor. In a chromatographic reactor (column), it is possible to utilize this property of the catalyst to separate different components and thus to achieve higher conversion of methyl formate than the equilibrium conversion of the reactant feed, on one hand by preventing the reverse reaction of formic acid and methanol and on the other hand by shifting the reaction towards the products by removing product components from the reaction mixture.

Furthermore, the above-described separation of the catalyst material needed in the stirred reactor is not necessary, because the reaction solution flows through a solid, stationary bed of the ion exchange resin. In the solution according to the invention, it is also noteworthy that high conversions can be achieved even at room temperature.

By carrying out the hydrolysis in a continuously operating multicolumn system, it is possible to achieve greater conversion, better separation of the reaction components, more economic use of different solutions, and thereby better productivity of the process. In such a system, the points of inlet and outlet of different flows are moved from one ion exchange bed to another in such a way that separate compounds are obtained as the output, particularly formic acid, in as pure and concentrated continuous product flows as possible.

In the solution according to the invention, the expensive and complex separation of reaction products, which is typical for processes of prior art, is simplified and facilitated, and the energy consumption of the separation stage can be reduced. Furthermore, the energy consumption of the separation stage can be further reduced by using instead of water one of the reactants as an eluent in the system, namely methyl formate, wherein the amount of water in the reaction mixture can be considerably reduced.

BRIEF DESCRIPTION OF THE DRAWINGS

In the following, the invention will be described in more detail with reference to the appended drawings, in which

FIG. 1 shows a method for preparing formic acid, in which the method of the invention is utilized. In the process, it is possible to distinguish between a reaction part in which methyl formate is prepared from methanol, a hydrolysis and separation part in which the hydrolysis of methyl formate and separation of formic acid from the reaction products take place, and a concentration part in which formic acid is concentrated to a desired final concentration. The different parts are outlined with dash-and-dot lines, and the main process flow and the product flow are indicated with thick arrows. In the preparation process, the reaction stage takes place in a reactor 1, to which a carbon monoxide containing gas (about more than 90 vol-% carbon monoxide) and methanol dried in a methanol drier 2 are supplied. By the effect of potassium or sodium methylate acting as a catalyst, methyl formate is formed of carbon monoxide and methanol. The reaction is exothermic, and the reactor 1 should be cooled to keep the temperature within a suitable range. The pressure of the reactor is about 30 bar and the temperature is about 80 to 100° C. Hydrogen, which is present in the synthesis gas used as the raw material, acts in a way of an inert gas and it is discharged from the reaction e.g. to combustion. Also pure carbon monoxide can be used. Because the reaction is an equilibrium reaction, the product flow of the reactor contains some unreacted methanol. The product flow is led into a distillation column 3 in which the methanol is separated and returned back to the reactor 1 via the methanol drier 2. The product flow obtained from the top of the distillation column 3 is led to the next part of the process, the hydrolysis and separation part, which comprises ion exchange beds 5 coupled in series. Before the hydrolysis, water is added to the methyl formate, so that the input flow to be fed to the ion exchange bed 5 contains water and methyl formate in a suitable ratio. The hydrolysis takes place when methyl formate and water flow through the ion exchange bed 5, and the hydrolysis products, methanol and formic acid, are simultaneously separated.

Figure 1:
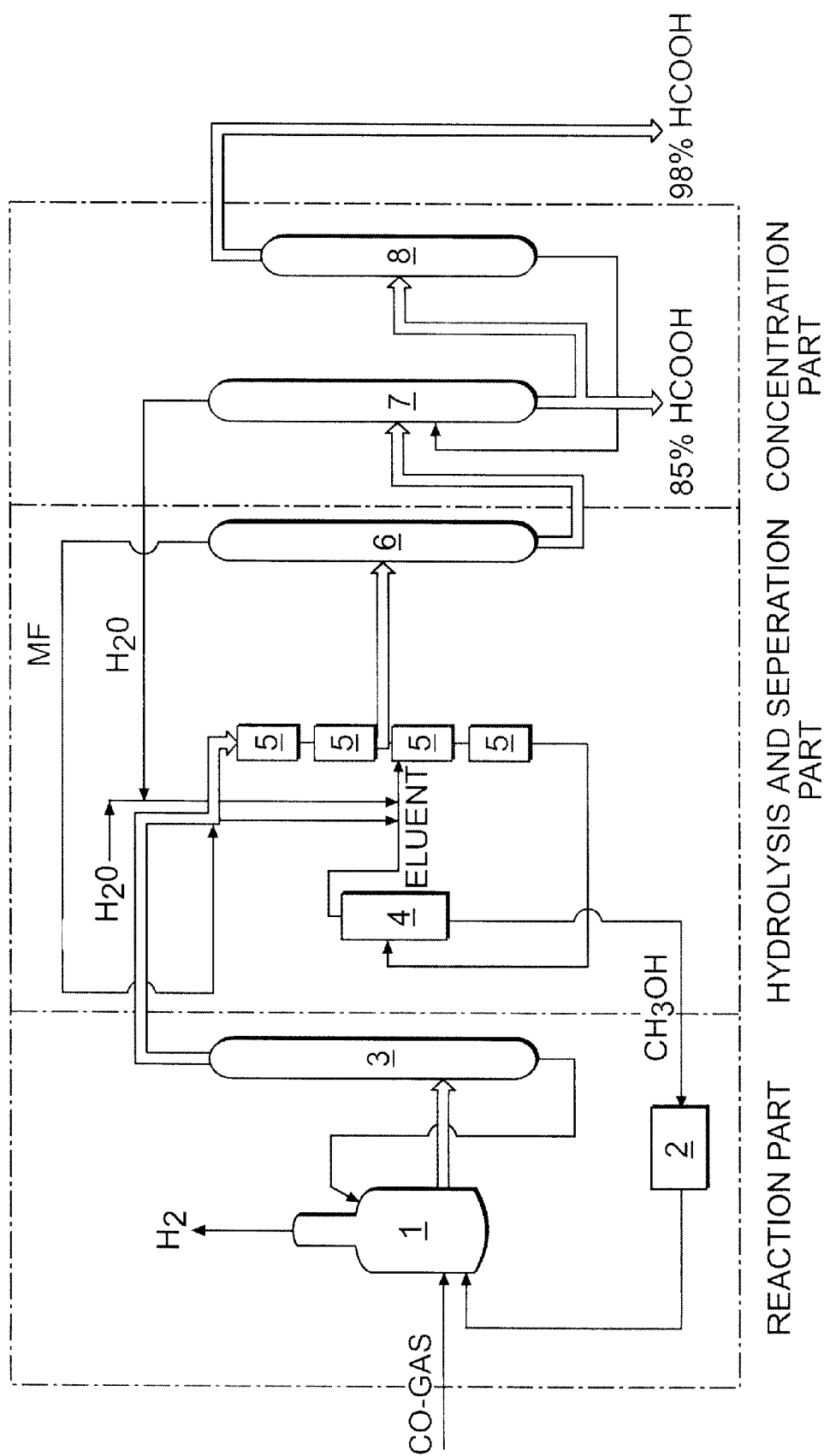
FIG. 1 shows an industrial process applying the method of the invention, starting from carbon monoxide and methanol.

By utilizing the separation properties in addition to the catalytic properties of the ion exchange material, two different flows with different compositions can be obtained from the ion exchange bed 5 or series of beds. These flows have different contents of formic acid and methanol in such a way that in the first flow, the formic acid content is greater than in the second flow, and in the second flow the methanol content is greater than in the first flow. The flows can be successive flows from the same ion exchange bed 5, obtained by pulse-like feeding; that is, the reactant mixture (methyl formate and water) is fed as a pulse of a certain length which is followed by an eluent with a different composition, e.g. pure water. This idea differs e.g. from the idea disclosed in EP patent 596 484, according to which the reactor filled with ion exchange resin is only used as a continuously operated hydrolysis reactor, whose product flow, remaining constant, is separately subjected to a separation process. According to one embodiment, ion exchange beds 5 are coupled in series in such a way that the inlet point of the input flow can be varied between different beds. Similarly, the outlet point of the output product flow can be varied, wherein the system comprises at least one, preferably two or more ion exchange beds that operate in the reaction step, i.e. the hydrolysis step. Methanol remained in the beds by adsorption is removed in a washing step with an eluent, and also the inlet point of the eluent and the outlet point of the methanol-containing eluent can be varied according to the bed/beds to be shifted to the washing step.

The output product flow will always contain methyl formate. This can be separated by feeding the product flow coming from the ion exchange beds 5 into a distillation column 6 in which methyl formate (and methanol) possibly left unadsorbed is separated from formic acid. The aqueous solution of formic acid is concentrated by distillation in successive distillation columns 7 and 8, and methyl formate (and methanol) obtained from the distillation column 6 is led to hydrolysis. The mixture of methanol and desorbent obtained from the washing stages is led to a distillation column 4 (methanol column), in which methanol is separated from the desorbent, and the desorbent can thus be circulated to the beds 5 that are in the washing step. Methanol can be led via the methanol drier 2 to the reactor 1.

The method is based on the catalyzing property of strongly acidic ion exchange resin as well as the differences in affinity between the ion exchange resin and the components of the reaction mixture; of the compounds produced in the hydrolysis reaction, methanol remains in the resin bed longer than formic acid.

In the hydrolysis and separation part of the method, two steps take place: the reaction step and the washing step. They both contain one or more ion exchange beds. In the reaction step, a desired quantity of the input mixture is run through the column. This is followed by the washing step, in which the bed is washed with water for a new reaction step.

In the reaction step, methyl formate and water react, whereby methanol and formic acid are produced. When flowing through the bed, methanol is adsorbed more strongly than formic acid onto the surface of the resin, wherein the methanol content of the mixture is reduced and the reaction will proceed further than the equilibrium value of the input. As a result, the content of the formic acid is increased. As a whole, the conversion of the reaction can be made higher and the reverse reaction is prevented when the methanol content is reduced. When the inlet location is moved from one bed to another in a series of several beds, the original input mixture can be made to react almost "to the full" and methanol can be concentrated in the column and formic acid concentrated in the eluent.

When the methanol content of the eluent issuing from the bed is low (and the reaction has proceeded sufficiently far), the eluent is taken as a product flow which contains a lot of formic acid and the eluent but little of the other reactant component and methanol. Because the methanol content of the product flow is low, no reverse reaction will take place when the eluent is separated from formic acid e.g. by distillation.

In the washing step, methanol is "washed" off the bed with the eluent in a countercurrent fashion with respect to the beds, wherein a methanol-rich eluent flow is obtained from the column which before the change of the column inlets had been an "input column" for the reaction stage. Methanol can be separated from the eluent by conventional methods, e.g. by distillation.

When methyl formate is used as the eluent, it is also possible to add some water to the eluent input in the washing step.

The flowcharts of the drawings illustrate the principle, and in practice, the output of products starts first after the "pure" eluent or reaction solution contained in the bed has been discharged from the bed and continues, if desired, also correspondingly in the column preceding the bed. The way of running depends on the number of beds, the desired purity of the product flow, etc.

The tests related to the invention were made in thermostatically controlled ion exchange columns at temperatures from 24 to 70° C. and under a maximum pressure of about 6 bar. A strong macroporous cation exchanger Amberlyst 15 was used in the tests. The quantity of the resin in the tests varied from 80 to 326 ml. The hydrolysis of methyl formate in the ion exchange bed can be carried out with both pulse-like and continuous feeding of the reactant mixture.

When pulse-like feeding is used, a certain quantity of the reactant mixture (methyl formate and water) is fed into the column, and it is flushed in forward direction in the bed with an eluent which is either of the reactants. In the pulse-like feeding mode, the duration of the pulse may vary to a great extent. In the tests made, it varied from 7 to 17.5 min. When the eluent is water, the different components are detected from the flow issuing from the bed as separate pulses in the following order according to the affinities between the components and the ion exchanger:

formic acid <methyl formate <methanol

The order is always the same with the same ion exchanger or adsorbent, but different factors can be used to influence the separation of peaks from each other and thus the purity of the product flows obtained. Such factors include e.g. the volume flow to the ion exchange bed, the duration of the feeding pulse (quantity of the reactant mixture), the length of the ion exchange bed, and the temperature. In continuous feeding, the starting solution is fed as a continuous flow into the bed, and after a certain time, the flow issuing from the bed is sets itself to the equilibrium composition. Before that it is possible to obtain, as a result of separation of the different components, a flow from the bed which is more concentrated with respect to formic acid than would otherwise be made possible by the equilibrium state according to the reactants.

The volume flow of the feeding solutions into the bed was within the range from 2.0 to 6.0 ml/min in both types of the tests. The hydrolysis of methyl formate is successful with both smaller and greater quantities of methyl formate with respect to water. In the tests, the methyl formate concentrations used varied from 32.4 to 73.9 wt-% which corresponds to water/methyl formate ratios of approximately 2:1 to 1:3.

EXAMPLE 1

Figure 2:
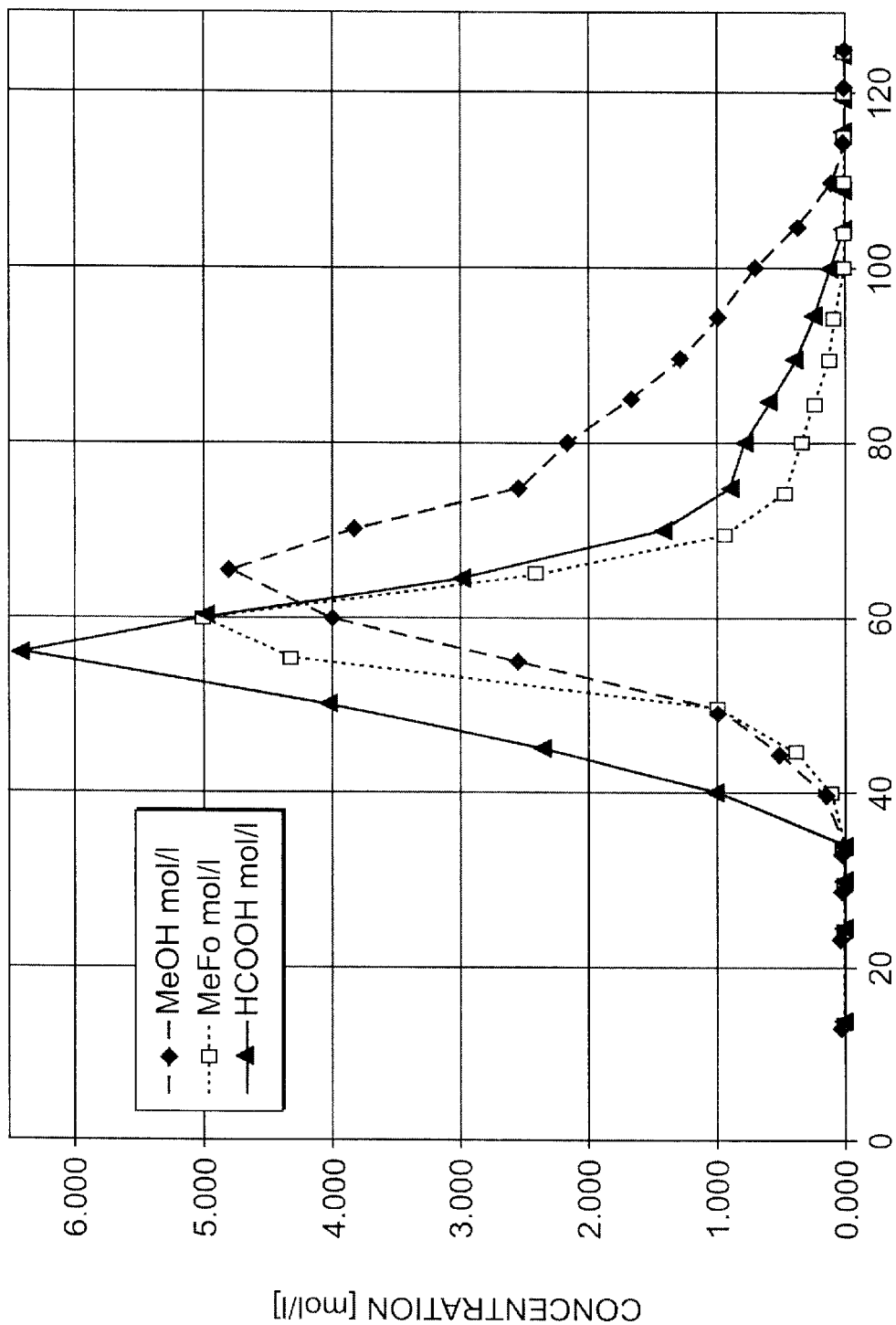
FIGS. 2–5 illustrate the effect of the ion exchange material in the hydrolysis and separation parts of the process.

In pulse feeding, when water was used as the eluent, at the best a formic acid concentration of 26.75 wt-% (6.4 mol/l) was achieved in the output, and the greatest achieved methyl formate conversion was 0.62. In this case the water content in the output flow was 48.97 wt-%. In these tests, the temperature was 38° C., the pressure was atmospheric pressure, and the water/methyl formate ratio was about 1:2. FIG. 2 shows the concentrations of methanol, methyl formate and formic acid in the flow issuing from the ion exchange bed.

EXAMPLE 2

Figure 3:
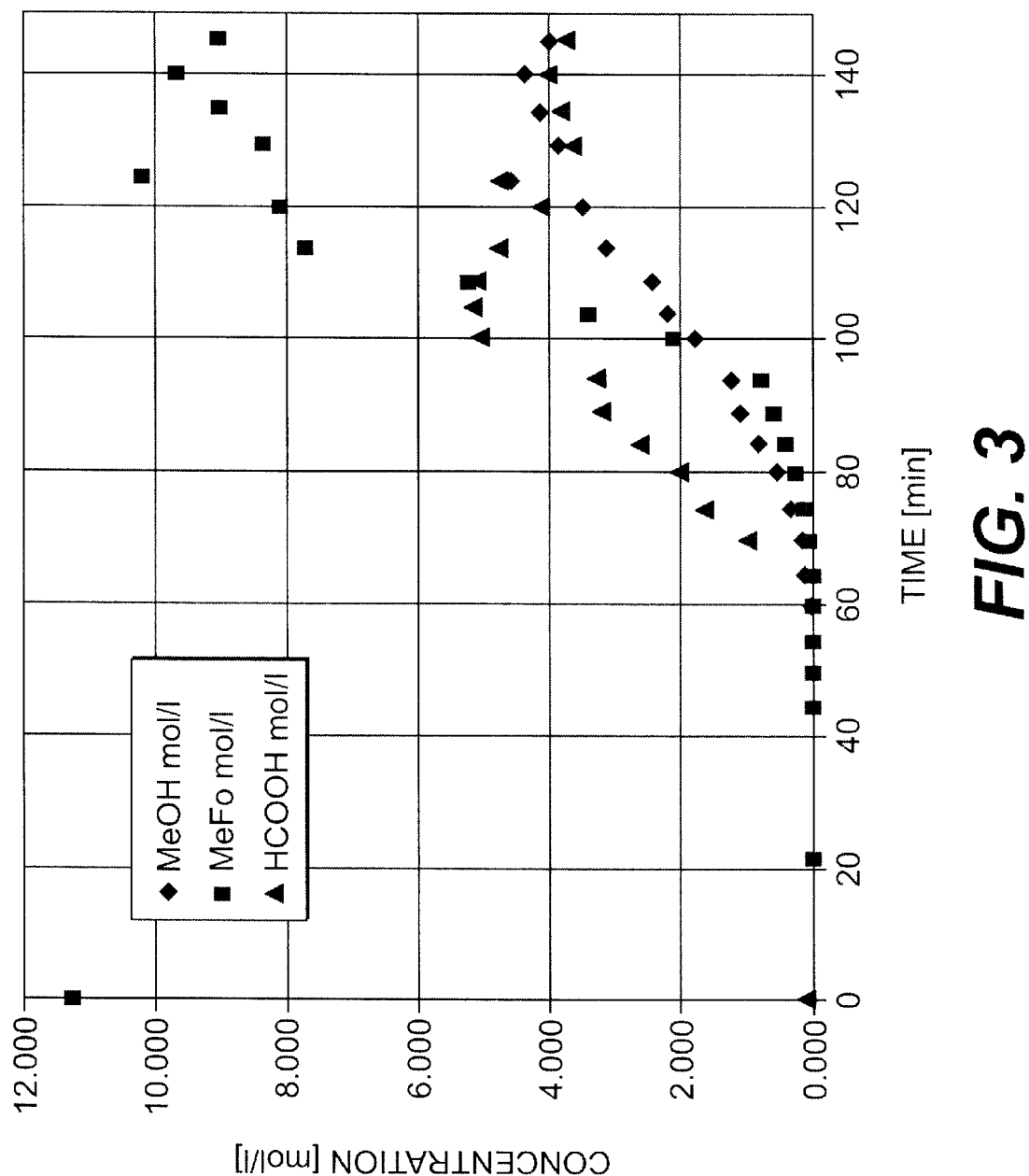

In continuous feeding, when water was used as the eluent, the greatest achieved formic acid content was 22.47 wt-% (5.1 mol/l) and conversion 0.69. In this case the water content was 42.43 wt-%. In this test, the temperature was 24° C., the pressure atmospheric pressure, and the water/methyl formate ratio about 1:2. FIG. 3 shows the concentrations of methanol, methyl formate and formic acid in the flow issuing from the ion exchange bed.

EXAMPLE 3

Figure 4:
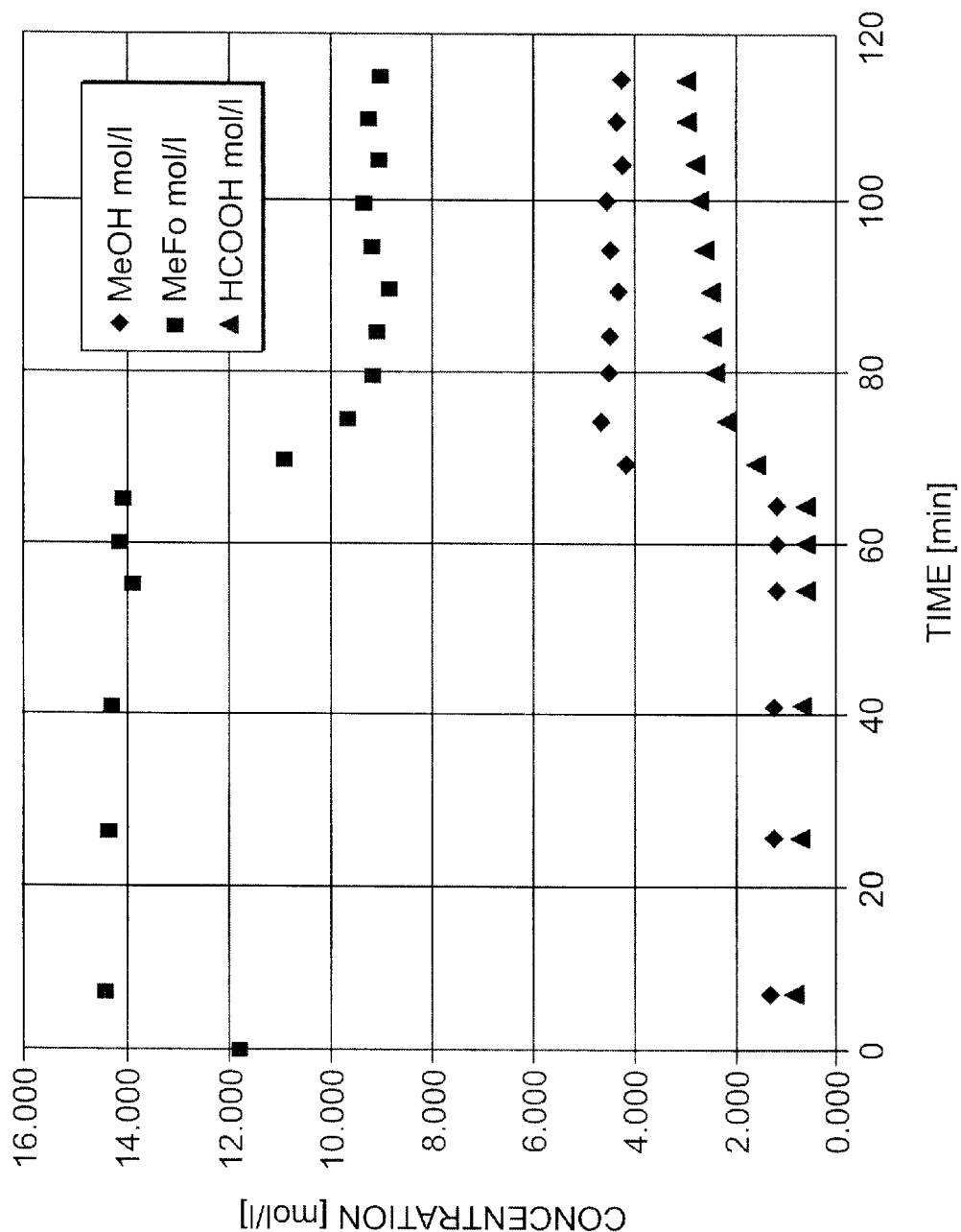

By using methyl formate as the eluent and by feeding the reactant mixture in a continuous flow, a conversion of 0.58 and a maximum formic acid concentration of 13.66 wt-% were achieved at room temperature, under atmospheric pressure, and with a water/methyl formate ratio of 1:2. In this case the water content was only 16.85 wt-%. FIG. 4 shows the concentrations of methanol, methyl formate and formic acid in the flow issuing from the ion exchange bed.

EXAMPLE 4

Figure 5:
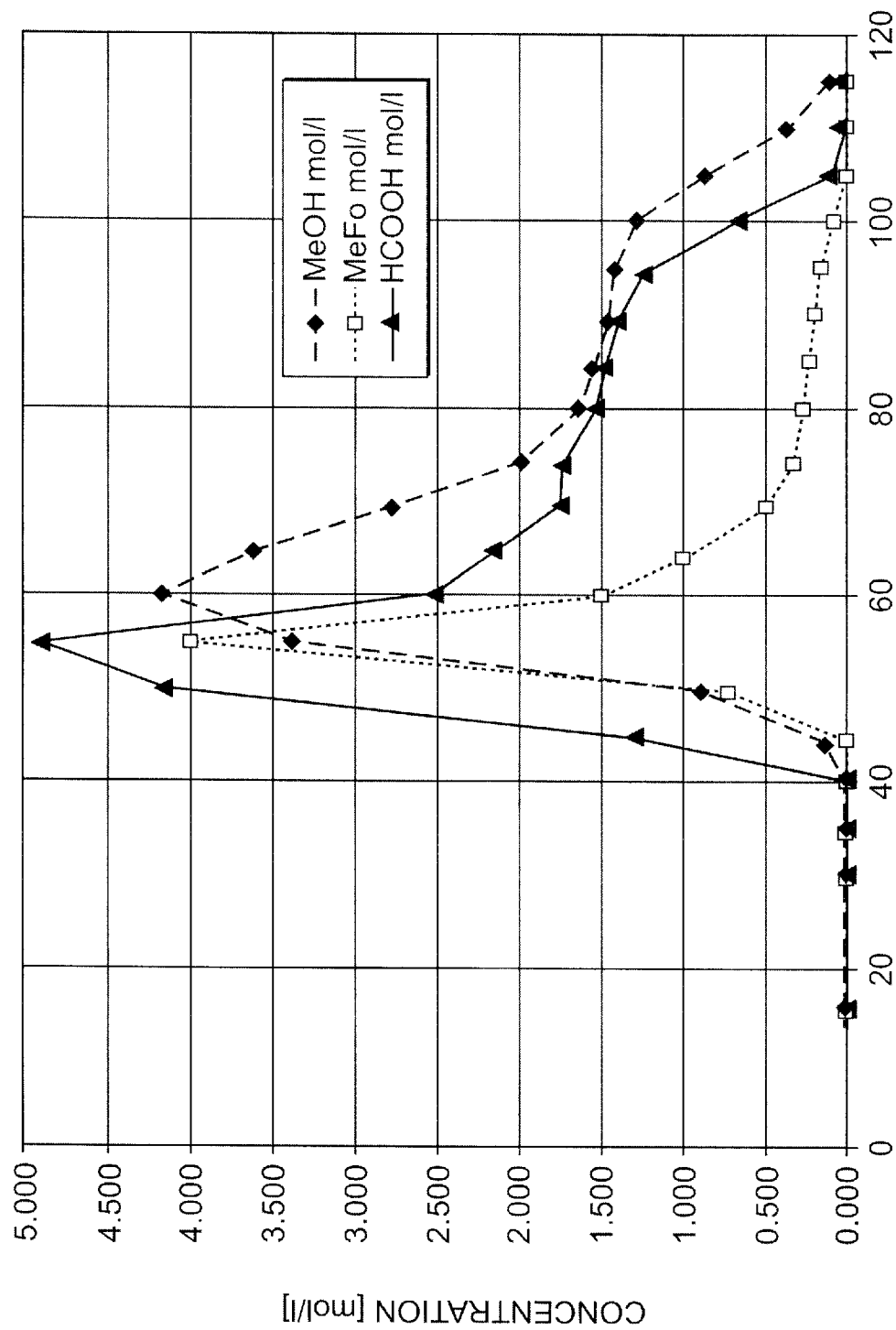

By performing the hydrolysis of methyl formate at a raised pressure of about 6 bar and a temperature of 70° C. with continuous feeding and using water as the eluent, the greatest formic acid concentration was 22.34 wt-% (4.9 mol/l) and conversion 0.78. In this case the water content was 42.21 wt-%. In the feeding, the ratio of water and methyl formate was about 1:3. FIG. 5 shows the concentrations of methanol, methyl formate and formic acid in the flow issuing from the ion exchange bed.

What is claimed is:

1. A method for preparing formic acid in which methyl formate is prepared with methanol as a reactant, methyl formate is hydrolyzed into formic acid and methanol, and formic acid obtained is seperated from methanol, characterized in that methyl formate obtained from methanol in a reaction (1) is fed through an ion exchange bed (5), in which the hydrolysis to formic acid and methanol and the separation of formic acid from the methanol take place simultaneously by means of the catalytic and absorbent properties of a solid ion exchange material in the ion exchange bed (5), when the reactant mixture containing water and methyl formate flows in one direction through the ion exchange bed and the hydrolysis of methyl formate and separation of formic acid from methanol take place by the effect of the same ion exchange material.

2. The method according to claim 1, characterized in that methanol obtained from the ion exchange bed is circulated back to the reaction (1), in which methyl formate is prepared.

3. The method according to claim 2, characterized in that methanol is separated from the flow obtained from the ion exchange bed (5) by distillation and recirculated.

4. The method according to claim 3, characterized in that the ion exchange material is an acidic cation exchanger, preferably a strongly acidic cation exchanger.

5. The method according to claim 1, characterized in that the temperature of the ion exchange bed (5) is from 20 to 120° C.

6. The method according to claim 5, characterized in that the pressure of the ion exchange bed (5) is in the range from 0 to 12 bar.

7. The method according to claim 1, characterized in that methanol remained in the ion exchange bed (5) is discharged from the ion exchange bed in a separate step after the reaction step by feeding the eluent through the ion exchange bed and methanol discharged from the bed is preferably circulated back to the reaction (1) in which methyl formate is prepared.

8. The method according to claim 7, characterized in that the eluent is fed into the ion exchange bed (5) both concurrently and countercurrently with respect to the feeding direction of the reaction step.

9. The method according to claim 8, characterized in that the eluent is water, methyl formate or a mixture which contains at least one of these components.

10. The method according to claim 8, characterized in that several different ion exchange beds (5) are used which are in different steps.

11. The method according to claim 10, characterized in that the ion exchange beds (5) are coupled in series, and the inlet point of the reaction step and the inlet point of the eluent are moved from one bed (5) to another.

12. The method according to claim 7, characterized in that the feeding to the ion exchange bed is performed in a pulse-like manner.

13. The method according to claim 1, characterized in that the product flow containing formic acid and obtained from the ion exchange bed (5) is led into one or more concentration steps.

14. The method according to claim 13, characterized in that the concentration is performed by distillation (7, 8).

* * * * *